United States Patent
Anderson et al.

[19]

[11] Patent Number: 6,080,581
[45] Date of Patent: Jun. 27, 2000

[54] CULTURE VESSEL FOR GROWING OR CULTURING CELLS, CELLULAR AGGREGATES, TISSUES AND ORGANOIDS AND METHODS FOR USING SAME

[75] Inventors: Charles Daniel Anderson, 3215 Jacquelyn Dr., Houston, Tex. 77054; Charlie W. Dodd, Seabrook, Tex.

[73] Assignee: Charles Daniel Anderson, Houston, Tex.

[21] Appl. No.: 09/415,975

[22] Filed: Oct. 12, 1999

Related U.S. Application Data

[62] Division of application No. 09/109,492, Jul. 2, 1998, Pat. No. 5,989,913.

[51] Int. Cl.$^7$ ............................................. C12M 15/00
[52] U.S. Cl. ......................................... 435/394; 435/420
[58] Field of Search ................................. 435/325, 383, 435/393, 394, 420, 286.3, 286.7, 289.1, 293.1, 299.1, 297.2, 298.2

[56] References Cited

U.S. PATENT DOCUMENTS

| | | | |
|---|---|---|---|
| 4,988,623 | 1/1991 | Schwarz et al. | 435/286 |
| 5,026,650 | 6/1991 | Schwarz et al. | 435/286 |
| 5,153,131 | 10/1992 | Wolf et al. | 435/240.24 |
| 5,153,132 | 10/1992 | Goodwin et al. | 435/240.24 |
| 5,153,133 | 10/1992 | Schwarz et al. | 435/240.24 |
| 5,155,034 | 10/1992 | Wolf et al. | 435/240.24 |
| 5,155,035 | 10/1992 | Schwarz et al. | 435/240.24 |
| 5,308,764 | 5/1994 | Goodwin et al. | 435/240.24 |
| 5,330,908 | 7/1994 | Spaulding | 435/240.24 |
| 5,376,548 | 12/1994 | Matsuo et al. | 435/284 |
| 5,437,998 | 8/1995 | Schwarz et al. | 435/286 |
| 5,449,617 | 9/1995 | Falkenberg et al. | 435/240.25 |
| 5,523,228 | 6/1996 | Ingram et al. | 435/240.25 |
| 5,665,594 | 9/1997 | Schwarz et al. | 435/394 |
| 5,702,941 | 12/1997 | Schwarz | 435/243 |
| 5,763,279 | 6/1998 | Schwarz et al. | 435/383 |

*Primary Examiner*—David A. Redding
*Attorney, Agent, or Firm*—Frank S. Vaden, III; Felsman, Bradley, Vaden, Gunter & Dillon, LL.P.

[57] ABSTRACT

A bioreactor system for culturing cells, cellular aggregates, tissues and organoids and methods of using same includes a cylindrical reactor vessel having an unobstructed longitudinal axis that is rotated about that horizontal axis to suspend cells and/or tissue in a culture medium. Filters are used within the vessel to retain the cells and/or tissues within the culture chamber and may be also used to subdivide the culture chamber. A pump maintains a flow of oxygen rich culture medium through the vessel to sustain cell respiration. A gas exchange device maintains desired gas concentrations in the medium and the entire system is operated within an enlarged incubator to maintain appropriate temperatures. Access ports on the vessel are used to introduce various materials into the culture chamber and to remove bubbles that may form in the medium. Sensors and a microprocessor unit monitor operational conditions and direct adjustments to maintain desired conditions.

Several methods of operating the bioreactor system are also disclosed wherein the vessel is used to culture cells, to grow three dimensional cellular aggregates and tissues, to filter waste materials and toxins from fluids, to commercially produce various biological materials from cells and/or tissue, and as a diagnostic or research tool.

3 Claims, 5 Drawing Sheets

CULTURE VESSEL FOR GROWING OR CULTURING CELLS, CELLULAR AGGREGATES, TISSUES AND ORGANOIDS AND METHODS FOR USING SAME

This application is a division of U.S. Ser. No. 09/109,492, filed Jul. 2, 1998, by Charles Daniel Anderson and Charlie W. Dodd entitled "Culture Vessel for Growing or Culturing Cells, Cellular Aggregates, Tissues and for Using Same", now U.S. Pat. No. 5,989,913.

FIELD OF THE INVENTION

This invention relates to an apparatus and method of use for a new culture vessel or bioreactor. The vessel is useful for growing cell cultures growing three dimensional cellular aggregates or tissues, for carrying out various cellular processes with tissues and/or organoids and for diagnostic testing and research.

BACKGROUND OF THE INVENTION

Bacterial cell culture processes have been developed for the growth of single cell bacteria, yeast and molds which can be characterized as encased with a tough cell wall. Large scale culture of bacterial type cells is highly developed and such culture techniques are less demanding and are not as difficult to cultivate as mammalian cells. Bacterial cells can be grown in large volumes of liquid medium and can be vigorously agitated without any significant damage.

Mammalian cell culture and tissue generation, however, is much more complex because such cells are more delicate and have a more complex nutrient requirement for development. Mammalian cells cannot withstand excessive turbulent action without damage to the cells and must be provided with a complex nutrient medium to support growth. Therefore, bioreactors with internal moving parts or obstructions will subject mammalian cells to high fluid shearing forces that will damage the cells. In addition, bioreactors that utilize mechanical parts, air or fluid movement as a lift mechanism to achieve particle suspension will likewise cause damage to growing cells and tissues due to fluid shear.

A primary use of bioreactors is in research where large numbers of cells are grown to refine the minute quantities of an active material (e.g. proteins) that the cells might secrete. Another use of bioreactors is the scale-up of laboratory cell culture processes for commercial purposes to mass produce the active proteins made by genetically engineered cells and tissues. Because of the need to culture mammalian cells in the laboratory in large quantities, bioreactors and culturing vessels have become an important tool in research and production of cells that produce active proteins.

A current problem in tissue culturing technology is the unavailability of an effective bioreactor for the in vitro cultivation of cells and explants that allows easy access to the materials contained in the vessel. Several devices presently on the market have been used with only limited success since each has limitations which restrict usefulness and versatility. Further, no bioreactor or culture vessel is known that will allow for the unimpeded growth of three dimensional cellular aggregates or tissues.

Cell culturing devices range upward in complexity from the petri dish to sophisticated computer controlled bioreactors. In the past, manufacturers have promoted various technologies to culture cells in the laboratory. For instance, simple adaptations of fermentors or stirred tanks used for the culture of bacteria, were marketed previously as the answer to culturing delicate mammalian cells. One of the principal factors limiting the performance of these systems is their inability to minimize turbulence due to stirring, i.e., shear due to fluid flow, and hence preventing free form association of cells in three dimensions.

PRIOR ART

A variety of methods and devices have been developed around the concept of horizontally rotating vessels for the suspension of solids in liquid media. Examples of such devices include bioreactors for cell culture as shown in FIGS. 1–3. Patents on such devices include, U.S. Pat. No. 5,155,035, issued to Schwarz et al., and entitled "Method For Culturing Mammalian Cells In A Perfused Bioreactor"; U.S. Pat. No. 5,155,034, issued to Wolf et al., and entitled "Three Dimensional Cell To Tissue Assembly Process"; U.S. Pat. No. 5,153,133, issued to Schwarz et al., and entitled "Method For Culturing Mammalian Cells In A Horizontally Rotated Bioreactor"; U.S. Pat. No. 5,153,131, issued to Wolf et al., and entitled "High Aspect Vessel And Method Of Use"; U.S. Pat. No. 5,026,650, issued to Schwarz et al., and entitled "Horizontally Rotated Cell Culture System With A Coaxial Tubular Oxygenator"; and U.S. Pat. No. 4,988,623, issued to Schwarz et al., and entitled "Rotating Bio-Reactor Cell Culture Apparatus." These patents are incorporated herein by reference as if set out fully verbatim. U.S. Pat. No. 5,153,132, issued to Goodwin et al., and entitled "Three Dimensional Co-Culture Process, is closely related to this group of patents and is also incorporated herein as if set out verbatim.

These prior patents disclose apparatuses that use either an internal cylindrical oxygenator or filter, as illustrated in FIG. 3, or a flat disk shaped oxygenator membrane inserted internally between the walls of the vessel, as illustrated in FIGS. 1 and 2 in cross section and elevation, respectively. Both types of vessels require oxygen transfer in order to sustain the growing cells.

Specifically, U.S. Pat. Nos. 4,988,623, 5,153,133, and 5,155,034 disclose culture vessels that allow three dimensional cell growth. These vessels are shaped similarly to each other due to a central tubular member that may either be an oxygenator that performs gas exchange through its surface, or it may be a cylindrical filter that allows the passage of an oxygen rich culture medium. The presence of a centralized tubular oxygenator or filter within a rotating vessel is a significant obstruction that will impede or prevent the growth of larger three-dimensional cellular aggregates. Further, in cases where a cylindrical filter has been used, it has been common to use internal blade members rotating about the central horizontal axis to move the fluid medium within the culture vessel. The use of such blades for mixing the culture medium has been found to be unneccessary and even detrimental due to the fluid shear that is caused by their rotation.

U.S. Pat. No. 5,153,131 discloses a bioreactor vessel without mixing blades or a central tubular membrane. This apparatus requires transfer of gases into the bioreactor vessel. As shown in the cross sectional view in FIG. 1, air travels through an air inlet passageway, through a support plate member, across a screen, and through a flat disk permeable membrane wedged between the two sides of the vessel housing. The oxygen then diffuses across the membrane into the culture chamber due to the concentration gradient between the two sides of the housing.

The rate at which oxygen can diffuse across the disk shaped membrane is a significant limitation that restricts the size of the culture chamber. Another disadvantage of the flat disk membrane in the '131 patent is that it is designed to flex in order to cause mixing within the culture chamber. This mixing effect is a feature that is described as being critical for the distribution of air throughout the culture media, however, it will also tend to create shear within the chamber.

Consequently, an improved apparatus and method for suspending particles (cells and their substrate) that minimizes fluid turbulence, while at the same time providing the required oxygen transfer, is needed to improve the performance of bioreactors. More specifically, there is a need for a bioreactor or culture vessel that provides sufficient internal space to grow large three-dimensional cellular aggregates while at the same time providing sufficient nutrients and gas exchange to sustain cell respiration and growth.

Providing sufficient gas exchange to sustain the growth of larger cellular structures is a significant restriction when designing a bioreactor or culture vessel. Attempts to overcome this problem have been directed in part at the use of gas permeable materials used to make these reactors. For instance, U.S. Pat. No. 5,702,941, issued to Schwarz et al., and entitled "Gas Permeable Bioreactor And Method Of Use" discloses a vessel that is horizontally rotated and is at least partially composed of gas permeable materials. The gas exchange with the culture medium is intended to occur directly through the gas permeable materials of which the vessel walls are composed. However, the specification of the '941 patent notes that the range of sizes for the vessel is still limited since gas exchange is dependent on the quantity of gas permeable surface area. It is emphasized that although the surface area of the vessel increases with the square of the dimensions, the volume of the vessel and thus, the internal culture medium, increases with the cube of its dimensions. As such, the preferred dimensions of the vessel described in the '941 patent are limited to between one and six inches in diameter while the width is preferably limited to between one-quarter of one inch and one inch. Such size limitations are not suitable for growing three-dimensional cellular aggregates and tissues.

Similarly, U.S. Pat. No. 5,449,617, issued to Falkenberg et al., and entitled "Culture Vessel For Cell Culture" discloses a vessel that is horizontally rotated. The vessel is divided by a dialysis membrane into a cell culturing chamber and a nutrient medium reservoir. Gas permeable materials are used in the vessel walls to provide gas exchange to the cell culturing chamber. However, the vessel is not completely filled with the nutrient medium and a large volume of air is maintained above the fluid medium in both chambers. The vessel is not designed to minimize turbulence within the cell culture chamber, rather mixing is recited to be essential to keep the dialysis membrane wetted. Further, the disclosure of the '617 patent does not contemplate using the vessel to grow cellular aggregates or tissues of any kind.

SUMMARY OF THE INVENTION

In the present invention, a cylindrical vessel with first and second end walls defines a cell culture chamber which is rotatable about an approximate horizontal axis. The first and second end walls are provided with an inlet and an outlet respectively for introducing an oxygen rich nutrient medium into and removing the spent medium and waste products from the vessel. Filters are located near the inlet and the outlet to prevent the passage of cells and cellular aggregates from the culture chamber while allowing the passage of the nutrient medium and cellular metabolic waste. The culture chamber is free of internal obstructions and structures that might cause fluid shear or that might otherwise impede the growth and/or suspension of large three dimensional cellular aggregates while the vessel is being rotated. A pump provides a constant flow of the nutrient medium through the chamber while the vessel is rotated and a gas exchange device is used to transfer gases into and out of the nutrient medium.

In another aspect of the present invention, the operation of the bioreactor system is automated by providing means for controlling the temperature of the vessel and/or nutrient medium. In addition, sensors monitor the flow rate, content, pH and temperature of the nutrient medium as well as the rate of rotation of the vessel. A microprocessing unit records data from such sensors and directs adjustments for maintaining the desired operation conditions within the culture chamber.

In another aspect of the present invention, additional filters may be used in the cylindrical vessel intermediate between the end walls to define or subdivide the culture chamber. Subdivision of the chamber is useful for growing different types of cells and cellular aggregates, for carrying out various cellular operations and functions and for conducting diagnostic research within the same cylindrical vessel. When the culture chamber is subdivided into multiple sub-chambers, access ports may be provided along the cylindrical wall of the vessel to provide access to each sub-chamber.

In another aspect of the present invention, the filter upstream relative to the direction of flow of nutrient medium through the culture chamber can be cylindrical in shape and located adjacent to but spaced apart from the cylindrical wall of the vessel so that fresh nutrient medium can enter the culture chamber and/or sub-chambers at all points along the length of the vessel. The filters of the present invention are made of a variety of materials and constructions and are chosen according to the application for which the vessel is to be used.

It is an object of the present invention, to provide a method for culturing cells and growing three dimensional cellular aggregates and tissues. The method includes the steps of filling a rotatable cylindrical vessel having a culture chamber with an unobstructed longitudinal axis with an oxygen rich fluid culture medium and introducing cells, cellular aggregates and/or tissues into the medium. A flow of oxygen rich fluid culture medium is maintained through the vessel to provide oxygen and materials to sustain cell respiration and growth and to remove cellular metabolic waste. The vessel is rotated about its horizontal longitudinal axis to suspend the growing cells and cellular aggregates in the medium. Periodically, the rotation of the vessel may be interrupted for the purpose of removing bubbles that may have formed in the nutrient medium and/or to remove materials from the culture chamber.

It is another object of the present invention to provide a method for filtering biological waste materials from a fluid medium using tissues or cellular aggregates to filter the waste materials from the medium. The method includes the steps of providing a rotatable cylindrical vessel having an interior chamber that is unobstructed along its horizontal longitudinal axis. The chamber is filled with an oxygen rich fluid culture medium and tissues and/or organoids are introduced into the medium. As used in this disclosure, the term organoid refers to a mass or aggregate of cells that mimics the structure and/or function of a tissue or organ. A flow of oxygen rich fluid culture medium is maintained through the vessel to sustain the organoids and to remove cellular metabolic waste. The organoids are suspended in the medium by the rotation of the vessel. A fluid containing the waste materials is then passed through the chamber and the organoids remove the waste by various cellular mechanisms. Additional cylindrical vessels can be connected in series to form a continuous chain of rotating vessels. Periodically, each vessel is replaced with another vessel containing fresh organoids.

It is yet another object of the present invention to provide a bioreactor vessel that is disposable. Due to the present bioreactor's simple design and construction, it can be easily and economically manufactured. The resulting bioreactor is consequently affordable, disposable, and may be mass produced. In situations where minimization of contamination is necessary, disposability of the bioreactor is a particular advantage. While the bioreactor may be produced in a wide variety of sizes, its simple construction provides the added advantage of allowing the reactor vessels to be made smaller than previously possible. The smaller sizes are particularly useful in research laboratories. In the alternative, the features of the bioreactor system of the present invention enable the growth of cells and cellular aggregates in larger volumes of media than was possible with prior art vessels. These larger volumes are particularly useful in the commercial scale production of biological materials.

Further aspects and objects of the present invention include providing a device and method for growing cells and tissues for replacement of defective and damaged tissues in humans and other animals, providing a device and method for growing cells and tissue cultures for the production of biological products such as but not limited to growth factor proteins, enzymes, platelets and genetically engineered materials, and providing a device and method for growing cells and tissue cultures for diagnostic procedures such as identifying and testing chemotherapy and other biochemical agents.

BRIEF DESCRIPTION OF THE DRAWINGS

So that the manner in which the above-recited features, advantages and objects of the invention, as well as others which will become apparent, are attained and can be understood in detail, more particular description of the invention briefly summarized above may be had by reference to the exemplary preferred embodiments thereof which are illustrated in the appended drawings, which form a part of this specification. It is to be noted, however, that the drawing illustrate only typical preferred embodiments of the invention and are therefore not to be considered limiting of its scope as the invention may admit to other equally effective embodiments.

In the Drawings

DESCRIPTION OF THE PREFERRED EMBODIMENTS

Figure 1:
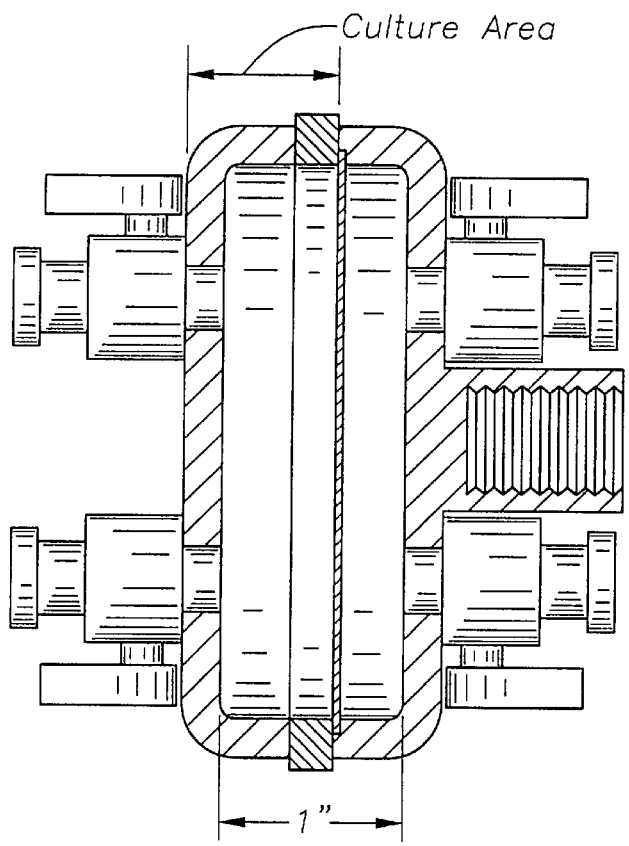
FIG. 1 is a partial cross sectional view of a reactor vessel known in the prior art showing the size limitation of such devices.
Figure 2:
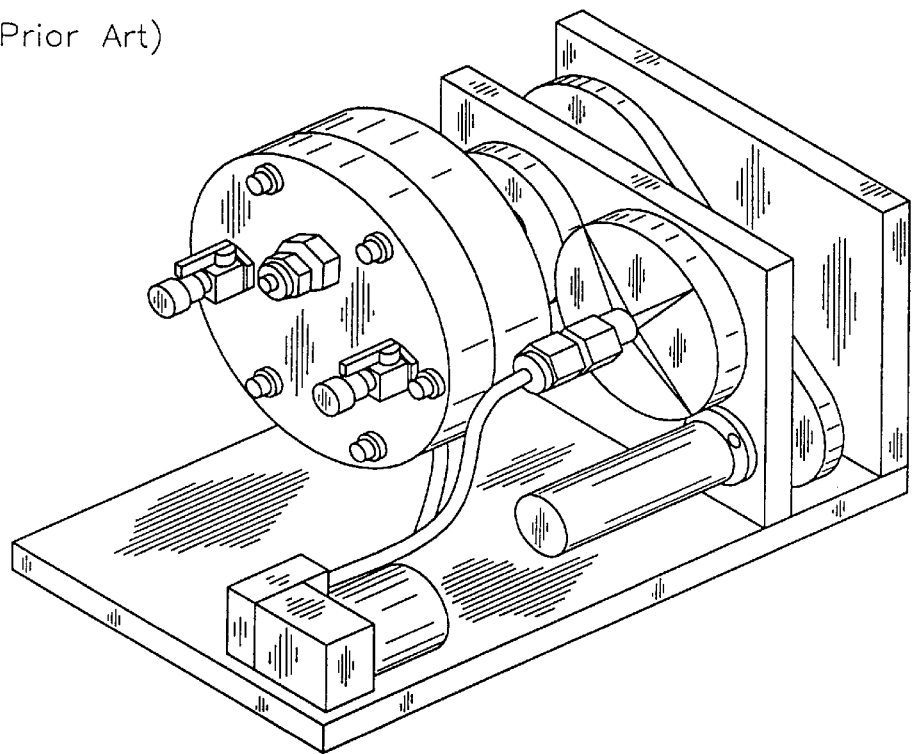
FIG. 2 is an elevated view of the prior art reactor vessel illustrated in FIG. 1, as mounted on a base having rotation means and gas exchange means.
Figure 3:
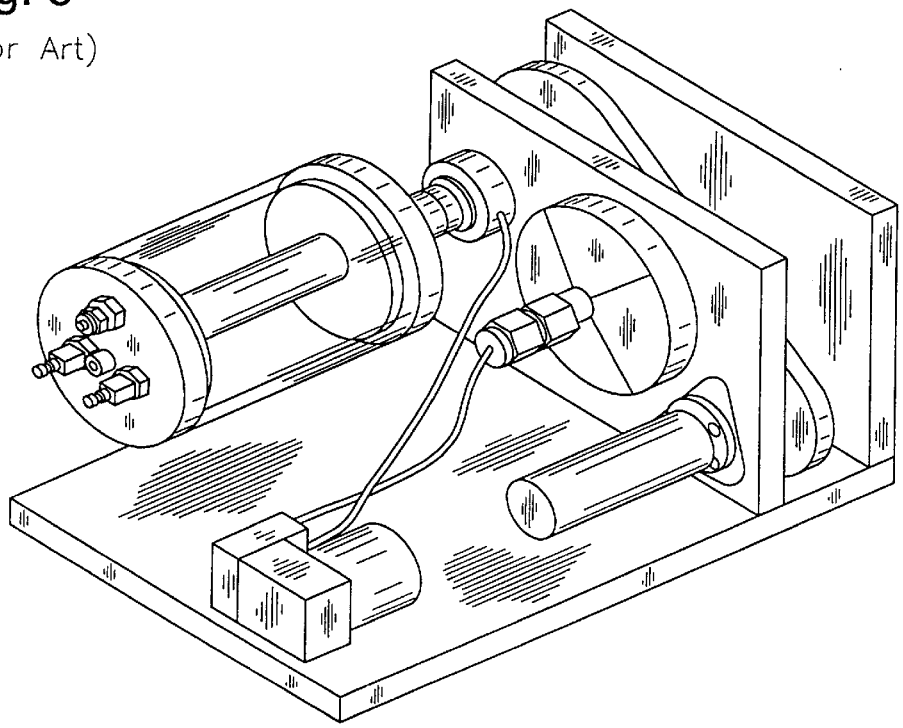
FIG. 3, is also a perspective view of a prior art device that has an elongated growth chamber, but which provides oxygen injection through a centrally disposed cylindrical membrane.
Figure 4:
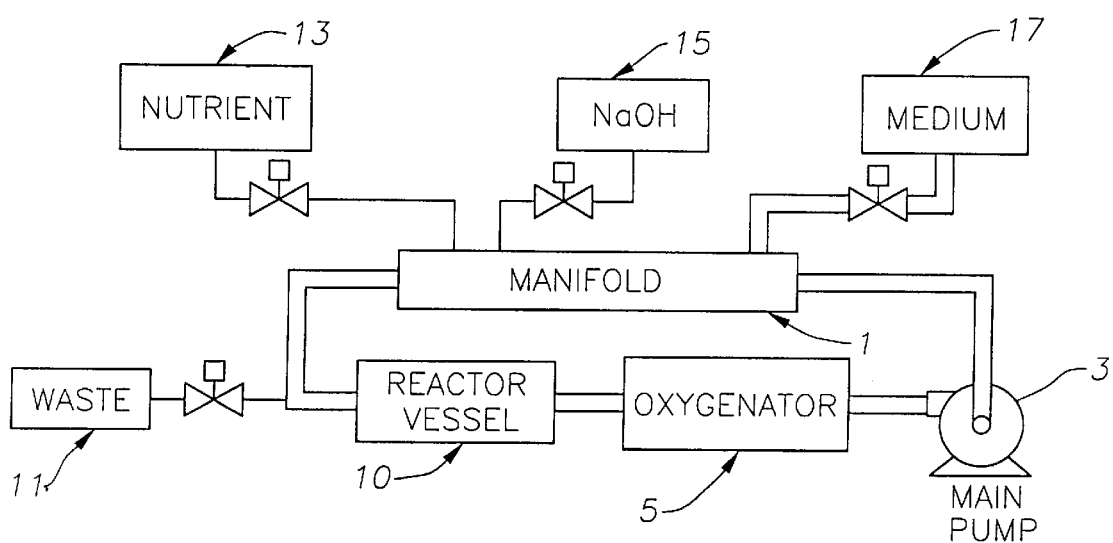
FIG. 4, is a flow diagram illustrating the fluid flow in an apparatus of the present invention.

Referring now to FIG. 4, in the overall system illustrated, a main fluid flow loop for growing mammalian cells includes a rotating cell culture reactor vessel 10, a gas exchange device or oxygenator 5, a main pump 3, and a supply manifold 1 for the selective input of nutrients, acids, bases, buffers and fresh medium to the circulating fluid nutrient medium.

In a preferred embodiment of the invention, reactor vessel 10 is made of a cylindrical vessel with first and second end walls, multiple filter elements and an unobstructed horizontal longitudinal axis defining an unobstructed culture chamber. The vessel has an inlet and an outlet, one or more vessel access ports for transferring materials into and out of the vessel as well as means for removing bubbles from the nutrient medium. The bioreactor system will have pump 3 for maintaining a flow of nutrient medium through the vessel, gas exchange device 5 for dissolving gases into and removing waste gases from the nutrient medium, and means for rotating the vessel about its horizontal axis. The bioreactor may also be provided with temperature control means, various sensors for monitoring the operational conditions and a microprocessor unit (not shown) for automating the operation of the bioreactor system.

Figure 5:
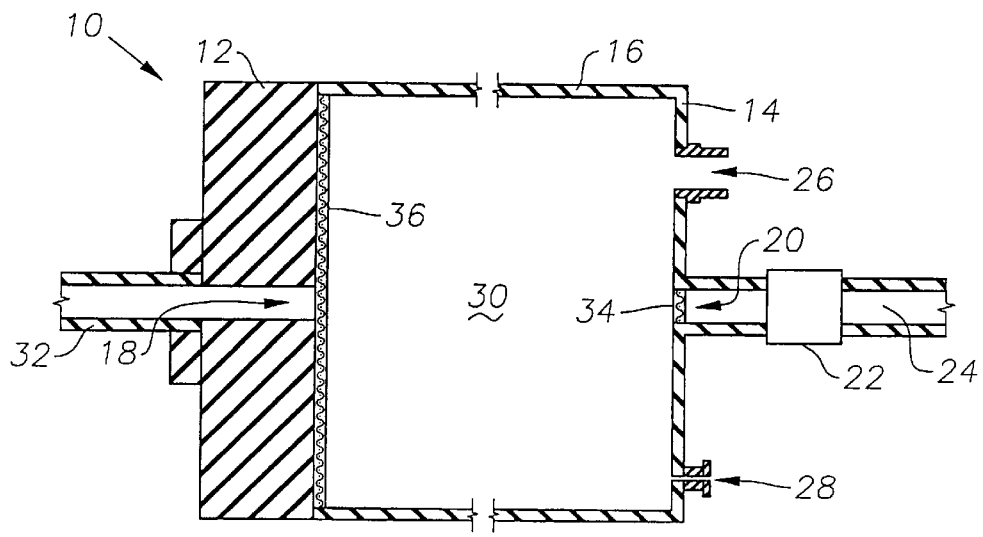
FIG. 5, is a cross sectional view of a reactor vessel of the present invention wherein the first filter is incorporated into the inlet.

Referring to FIG. 5, materials used to construct cylindrical wall 16 of vessel 10 will preferably be a transparent, non-toxic, biocompatible material such as glass or a clear plastic. Most preferably, the clear material is a polycarbonate such as LEXAN® (a registered trademark of General Electric). The end walls will preferably be a material that is both durable and machines well. Most preferably, the end walls will be manufactured from an acetal polymer such as DELRIN® (a registered trademark of E. I. du Pont Nemours & Co., Inc.). Cylindrical wall 16 and end walls 12 and 14 may be formed by injection molding, wherein various parts of the bioreactor vessel 10 may be welded, glued or mechanically attached together.

End walls 12 and 14 and cylindrical wall 16 may also be gas permeable. When desired, these structures may be made of a variety of materials such as silicone rubber, polytetrafluroethylene, polyethylene, porous plastic coated with a hydrophobic material, mixtures of silicone with other plastics, and silicone rubber coated cloth. When gas permeability is desired, preferably, the cylindrical wall 16 is constructed of a porous plastic coated with a hydrophobic material on the interior surface. Most preferably, the cylindrical wall 16, is made of porous hydrophobic Teflon® (a registered trademark of E. I. du Pont Nemours & Co., Inc.) when gas permeability is desired.

The cylindrical wall 16 may be made in any size provided that adequate nutrients and gases can reach the growing cells and cellular aggregates within the culture chamber. The size of the vessel is therefore limited only by the flow rate of the fluid nutrient medium into the culture chamber and the contents of that medium. The prior art discloses reactor vessels that have a culture chamber with a length of at least 0.25 inches but no more than 1 inch. The preferred volumes of these prior art vessel chambers is generally less than 500 ml. However, when sufficient nutrient flow is provided through the culture chamber within vessel 10 of the present invention, the length and diameter of cylindrical wall 16 will be much larger than the dimensions of these prior art bioreactors. More specifically, because the culture chamber of the present invention has maximum dimensions that are determined by the flow rate and content of the fluid medium that passes through the culture chamber, the culture chamber can have maximum lengths well in excess of 1 inch and can have internal volumes up to 100 liters.

The end walls of vessel 10 include first end wall 14 and second end wall 12. The nutrient medium flows through the vessel generally in only one direction and as such, the ends of the vessel are periodically referred to as upstream and downstream, respectively. However, as noted below, the flow of the nutrient medium may be periodically reversed, and thus, the end walls are more generally referred to as first and second end walls.

In FIG. 5, first end wall 14 is connected to the upstream end of cylindrical wall 16 to form the upstream portion of vessel 10. The cylindrical wall and the two end walls may be glued, welded or mechanically attached to one another to form vessel 10. First end wall 14 is provided with inlet 20 that is coupled via rotative coupling 22 to conduit 24. First end wall 14 is shown with only a single inlet 20. However, it is anticipated that conduits may be machined into end wall 14 to provide additional inlets into the culture chamber at various locations on the end wall. More specifically, radially oriented bores may machined into the end wall so that a plurality of inlets is arranged about the periphery of end wall 14. Such an arrangement of inlets provides a greater distribution of the oxygen rich nutrient medium as it enters the culture chamber through end wall 14.

The inlet or inlets of end wall 14 are in fluid communication with conduit 24 which is in fluid communication with gas exchange device 5. As shown in FIG. 4, main pump 3 provides fresh nutrient medium to the gas exchange device wherein the nutrient medium is oxygenated and passed on to vessel 10. The return spent nutrient medium from vessel 10 is returned to manifold 1 where it receives a fresh charge of nutrients, acid, base, buffer, or liquid medium, as necessary before recycling. Adjustments to the nutrient medium may be made in response to chemical sensors suspended in the medium and/or to electrochemical sensors located within or down stream of vessel 10. The pH of the medium is corrected by controlling carbon dioxide pressures and introducing acids, bases and/or buffers. Dissolved oxygen, nitrogen and carbon dioxide are maintained in appropriate concentrations by gas exchange device 5 in order to support cell respiration. Spent medium may be directed to a waste or drain as it passes from the vessel. Alternatively, where the cells, cellular aggregates and/or tissues within vessel 10 are synthesizing and/or excreting materials that are to be retained, those materials may be directed to collection device 11.

Referring again to FIG. 5, first end wall 14 is provided with access port 26 for accessing the interior of the culture chamber. Although only a single port 26 is shown in the figures, additional access ports may be utilized depending on the particular application of the bioreactor. As shown in FIG. 5, the access port 26 provides access to the vessel for the input of medium and cells and for the removal of cultured cells and cellular aggregates. In the preferred embodiment, the vessel access ports are constructed with valved closure means or a septum-membrane closure. The valves preferably are plastic, but may be made of metal or any other material which is non-toxic, capable of being sterilized and is hard enough for machining into an access port. Further, access port 26 may be provided with a variety of couplings for connecting with various fittings. Where the culture chamber within vessel 10 is subdivided into sub-chambers, access ports may be provided along the length of the cylindrical wall 16 in order to allow access to each of the various sub-chambers.

Vessel 10 is also provided with means for trapping bubbles that may develop in the culture chamber and an adjacent port is provided for removing the bubbles from the bubble trapping means. As shown in FIG. 5, bubble removal port 28 is incorporated into first end wall 14. Although not shown, bubble trapping means may take a variety forms. For instance, a portion of the inner surface of cylindrical wall 16 may be provided with a recessed structure that is designed to trap bubbles during the rotation of vessel 10. Regardless of the structure that is used to trap bubbles, an access port such as bubble removal port 28 should be located adjacent to such means. Further, it is anticipated that bubble removal port 28 will have a valve type closure so that a hypodermic syringe may be attached to remove bubbles from the chamber so as to minimize turbulence that might be created during the removal of bubbles. Alternatively, a septum membrane type closure may also be employed.

Figure 9:
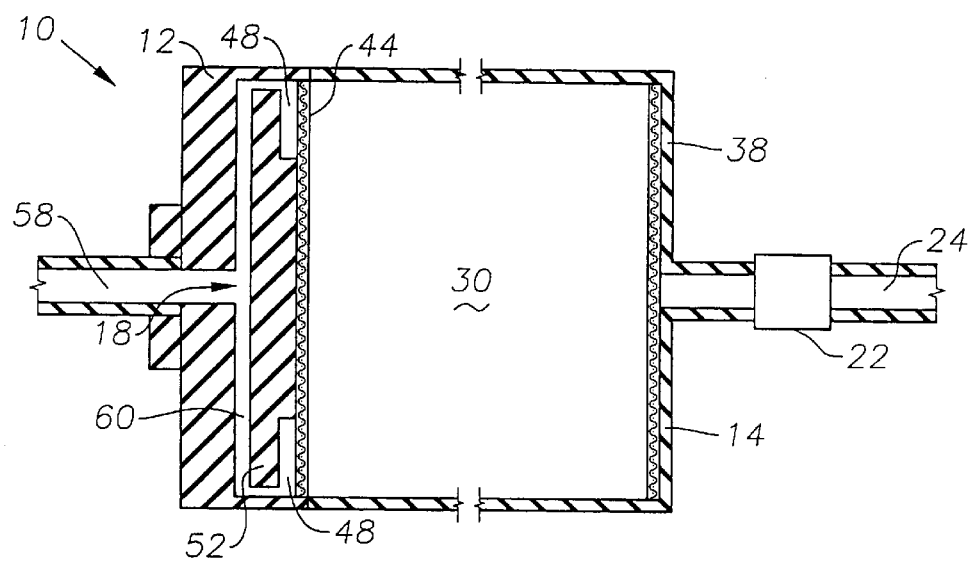
FIG. 9, is a cross sectional view of a reactor vessel of the present invention wherein multiple outlets are located about the periphery of the culture chamber.

Second end wall 12 is connected to cylindrical wall 16 to form the downstream portion of vessel 10. Second end wall 12 is provided with central outlet 18 and is connected to drive shaft 32. Drive shaft 32 is connected to means for rotating the shaft and the vessel as is discussed below. Alternatively, it is anticipated that means for rotating the vessel may be directly attached to either end wall or the cylindrical wall of the vessel. However, the balance of this description assumes that the rotation means is adapted to rotate the drive shaft 32 which is fixedly connected to the second end wall 12. Central outlet 18 is in fluid communication with conduit 58 for directing fluid medium away from the vessel. Second end wall 12 may have only central outlet 18 or it may have a plurality of outlets 48. As shown in FIG. 9, outlets 48 may be arranged about the periphery of vessel 10 with fluid communication with central outlet 18 provided via wall bores 60. Plurality of outlets 48 can have a variety of configurations as determined by the particular application of the bioreactor and the ease of manufacture.

Since the operation of the bioreactor of the present invention requires a constant flow of oxygen rich fluid nutrients through the vessel, filters are used define and subdivide the culture chamber and to retain the growing cells, cellular aggregates, tissues and/or organoids in the culture chamber. Therefore, the use of filters is preferred over dialysis membranes and the like. The filter should be of a size that allows the passage of sufficient oxygen rich nutrient medium to sustain cell respiration and growth while preventing the passage of cells, cellular aggregates tissues and/or organoids. The combination of such a filter with a constant flow of oxygen rich medium will sustain cellular respiration and growth within a much larger vessel than was previously known. Further, by providing a continuous flow of oxygenated nutrient medium, it is no longer necessary to periodically change the nutrient medium, a process that interrupts the rotation of the vessel and increases the risk of contaminating the culture or otherwise damaging the cells, cellular aggregates, tissues and/or organoids.

The filters used in the present invention may be made of a variety of materials having a variety of constructions provided that they have a porosity that allows the nutrient medium and cellular metabolic waste to travel through the filter but that will prevent the passage of cells and cellular aggregates. In particular, the filters of the present invention may be made of a polycarbonate film that has been irradiated to render it porous, polyester cloth and various woven materials such as a woven fabric of stainless steel. Such filters are commercially available from a variety of sources.

It is anticipated that filters made of biodegradable materials such as polyglycolic acid may also be used. In particular, there will be applications when the growth of cellular aggregates, tissues and/or organoids will either require a substrate or the use of a substrate will provide a desired shape or structure in the grown product. For such applications, a filter made of biodegradable material that will slowly degrade after the growing cells have attached to the upper surface of the filter is desirable.

The size, mesh and location of the filters can vary widely. The mesh size of the filter material or construction is determined in large part by the application for which the bioreactor system is to be used. If the reactor vessel is used to produce or test white blood cells the mesh size will need to be quite small to prevent the leukocytes from passing. If the vessel is being used to produce a bone marrow, a larger mesh size will be sufficient. Culture work concerning the production or testing of cellular aggregates such as tissues and organoids can utilize still larger mesh sizes.

Figure 6:
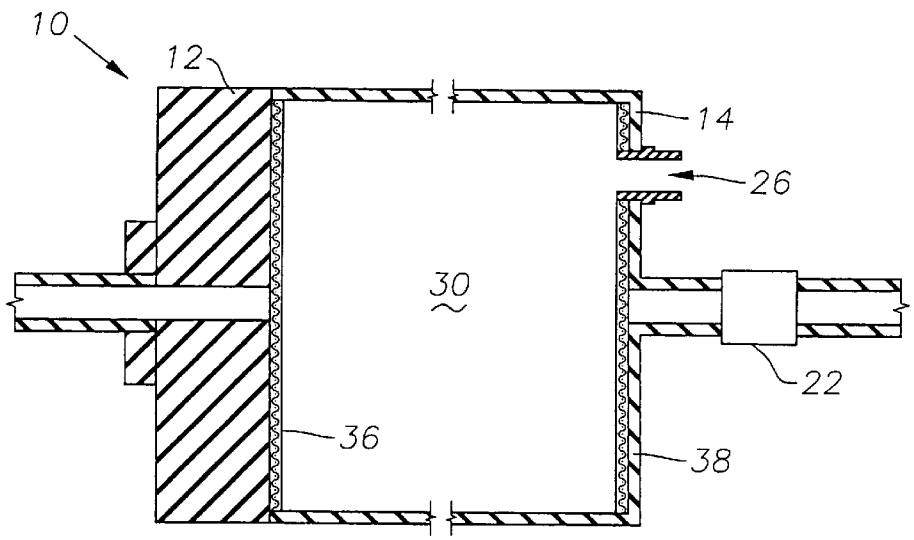
FIG. 6, is a cross sectional view of a reactor vessel of the present invention wherein the first filter is attached to the first end wall.

A first filter 34 should be used to prevent the cells and cellular aggregates in the culture chamber from travelling upstream from the reactor should the fluid flow through the reactor be reversed. As illustrated in FIG. 5, filter 34 can be a small filter fixed within inlet 20 or as shown in FIG. 6, can be arranged across the full diameter of the vessel attaching to end wall 14 and cylindrical wall 16 at its periphery. In addition, the filter elements may be sandwiched between the various components of vessel 10 such as between the end walls and the cylindrical wall as is shown in FIG. 12.

To improve the distribution of the nutrient medium to the culture chamber, filter 34 may have additional configurations.

Figure 12:
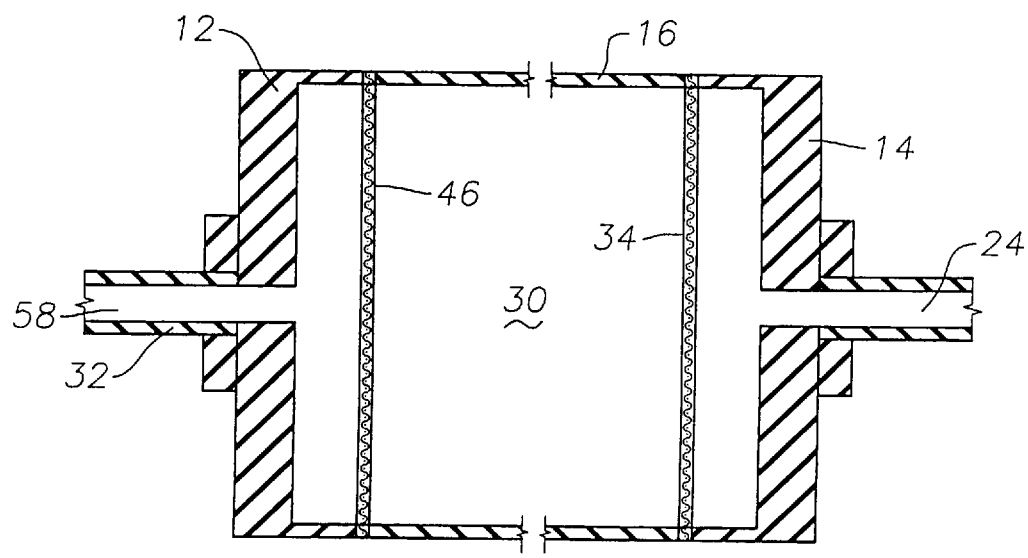
FIG. 12, is a cross sectional view of a reactor vessel of the present invention that is particularly useful for filtering waste materials and toxins from a fluid.

For instance, filter 34 may be attached about its periphery to the cylindrical wall 16 of the vessel, adjacent to but spaced apart from end wall 14 as shown in FIG. 12. In such a configuration, the nutrient medium enters vessel 10 through inlet 20 and passes across filter 34 at all points on the filter such that an improved distribution of medium is achieved.

Figure 7:
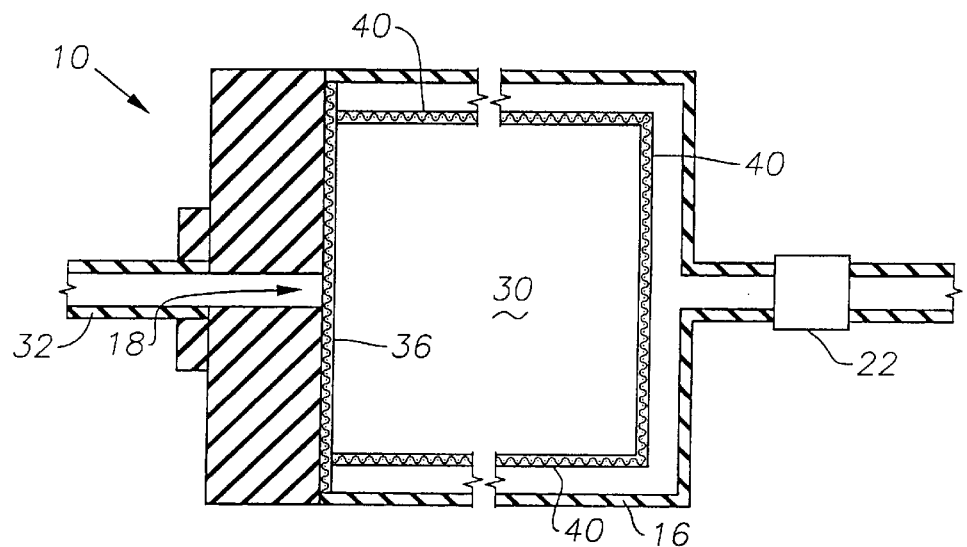
FIG. 7, is a cross sectional view of a reactor vessel of the present invention wherein the culture chamber is defined by a cylindrical filter adjacent to but spaced apart from the cylindrical wall of the vessel.
Figure 11:
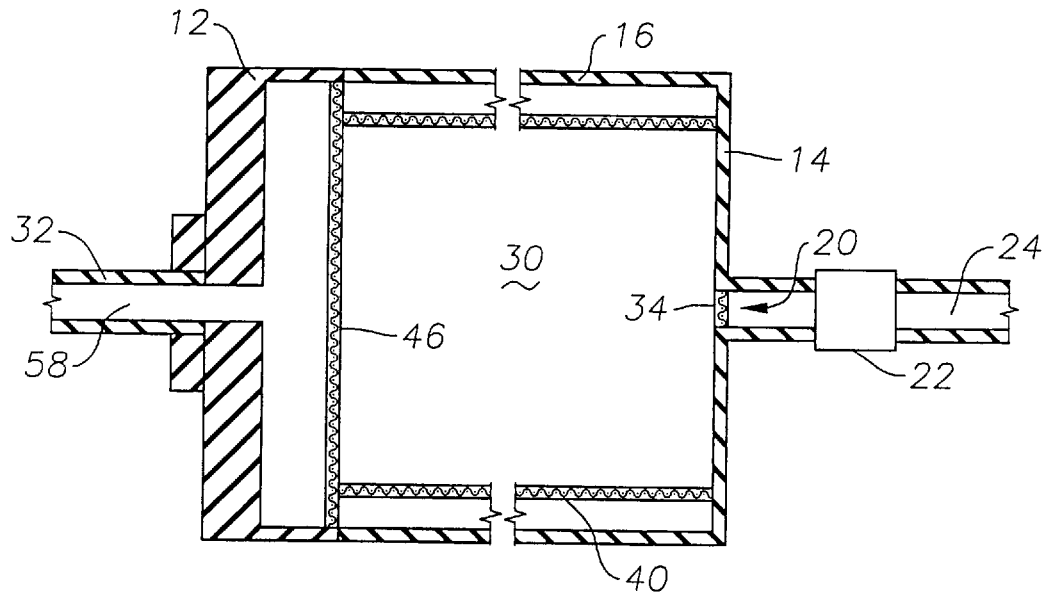
FIG. 11, is a cross sectional view of a reactor vessel of the present invention having a cylindrical filter along the length of the vessel and a downstream filter that is adjacent to but spaced apart from the second end wall of the vessel.

Additionally, as illustrated in FIG. 7, the upstream filter may be formed into cylindrical structure 40 and attached to downstream filter 36 to form a filter enclosed culture chamber 30. The particular advantage of cylindrical filter 40 is that the nutrient medium passes between cylindrical wall 16 and filter 40 and can thus pass through the filter directly into all parts of culture chamber 30 along the length of the vessel. As such, the nutrient medium is not required to pass through a series of chambers and/or filters to reach the downstream portions of culture chamber 30 or downstream subchambers. Alternatively, the flow of medium may be directed immediately into culture chamber 30 and out through cylindrical filter elements 40 as shown in FIG. 11. With such a configuration, upstream filter element 20 may be unnecessary in that it is unlikely that the cylindrical filter element 40 and downstream filter element 46 will simultaneously become clogged such that any back flushing would be required.

Figure 8:
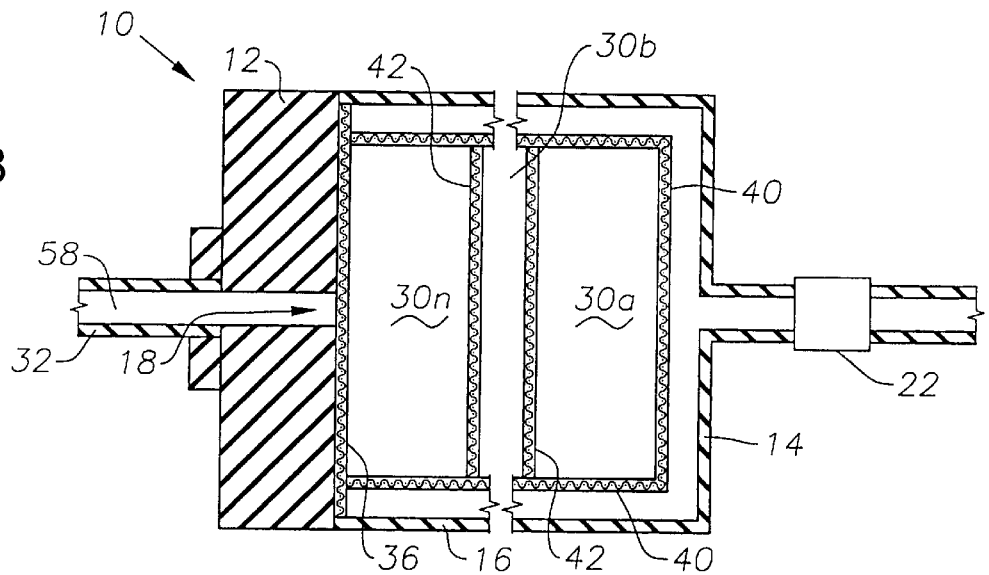
FIG. 8, is a cross sectional view of a reactor vessel of the present invention wherein the culture chamber is defined by a cylindrical filter and is subdivided into sub-chambers by additional filter elements.

FIG. 8 illustrates how the culture chamber may be subdivided into sub-chambers 30a, 30b and on out to 30n, where n is a positive integer greater than 1, by intermediate filter elements 42. Again, the advantage of this configuration is that nutrient medium can pass between cylindrical wall 16 and cylindrical filter 40 and provide fresh nutrient medium to each sub-chamber along the length of the vessel. Although not illustrated in the figures, cylindrical wall 16 can have access ports along its length to provide access to culture chamber 30 and to sub-chambers 30a–30n when the chamber is subdivided by intermediate filter elements 42.

Figure 10:
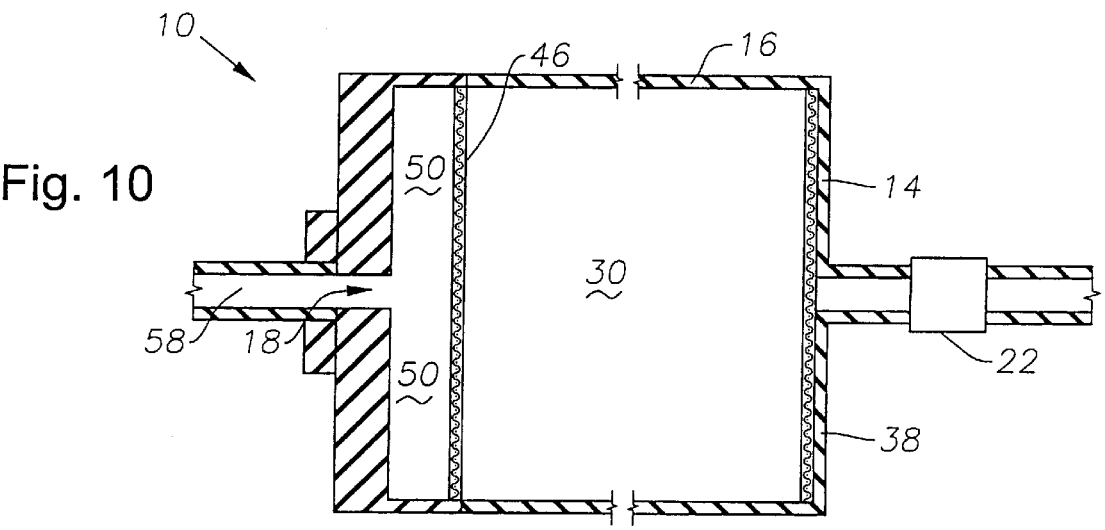
FIG. 10, is a cross sectional view of a reactor vessel of the present invention wherein the downstream filter is adjacent to but spaced apart from the second end wall.

In addition to those filter elements disposed upstream of and within culture chamber 30, a filter element downstream of the chamber is also required to prevent the cells, cellular aggregates, tissues and/or organoids from passing out of the vessel. Again, filter 36 can have a variety of configurations within and without vessel 10. As illustrated in FIGS. 5–6 and 7–8, filter 36 can be provided along the surface of second end wall 12. Alternatively, filter 36 may be arranged within outlet 18 (not shown) or attached about its periphery to cylindrical wall 16 and spaced apart from outlet 18 as illustrated in FIG. 10.

It is anticipated that filter 36 may periodically become clogged with cells and cellular aggregates. In such an instance, the direction of the flow of the nutrient medium should be reversed by pump 3 until the clog has been cleared. The direction of flow of the nutrient medium may also be reversed in order to cause the suspended cells, cellular aggregates and/or tissues to become attached to a substrate or the filter elements of the vessel.

As illustrated in FIG. 4, the bioreactor system is provided with pump 3 which maintains a flow of fluid nutrient medium through the vessel 10. Pump 3 may be a peristaltic pump or similar device that is capable of maintaining a relatively constant flow of fluid medium through the reactor vessel. Pump 3 may be adjusted to a variety of flow rates and is capable of reversing the direction of medium flow through the vessel.

The bioreactor system is also provided with gas exchange device 5. Gas exchange device 5 may be characterized as an oxygenator, but the device should be capable of maintaining desired gas concentrations for the variety of gases needed to sustain and promote cellular respiration. Oxygen is consumed in the culture chamber and carbon dioxide is given off as a byproduct of cellular respiration. Thus, the gas exchange device must be capable of transferring oxygen into and removing carbon dioxide from the nutrient medium. If not properly balanced, the increasing quantities of carbon dioxide will render the circulating medium acidic.

In the gas exchange device used in the present invention, gases are transferred into and out of the nutrient medium across a multi-layered cylindrical membrane composed primarily of silicone rubber. The cylindrical membrane is located in a cylindrical housing that has upstream openings for receiving the nutrient flow from the pump and downstream openings for passing the oxygen rich medium onto the reactor vessel. The housing is provided with a fan attached thereto to maintain a constant flow of air through the housing and across the surfaces of the cylindrical membrane.

The present invention involves the rotation of reactor vessel 10 about its central horizontal axis. This involves a type of clinostat principal, i.e. a principal that fluid rotated about a horizontal or nearly horizontal axis can effectively suspend particles in the fluid independent of the effects of gravity. The rotational speed of vessel 10 effectively eliminates the velocity gradient at the boundary layer between the fluid and cylindrical wall 16. Thus, shear effects caused between a rotating fluid and stationary wall are significantly reduced or eliminated.

The clinostat principal involved allows cells or cell aggregates having densities different from the fluid to travel in a nearly circular path and to deviate insignificantly from the fluid path. Relative to the rotating reference frame, the gravity vector is observed to rotate so that its average time is nearly zero. This allows for suspension of the particles in a carrier medium with low fluid shear and with low interference. Cylindrical wall 16 is rotated in order to reduce the adverse fluid velocity gradient through the boundary layer that would otherwise occur at the interface between the moving fluid and the fixed wall. The rotation of cylindrical wall 16 is sufficient to cause fluid rotation due to viscosity. The operating limits are defined by the sedimentation rate of the particles in the fluid medium and the acceptable centrifugal force due to rotation. Further, it is possible to vary the angular rotation rate in order to induce secondary flow patterns within the vessel which may be useful for distributing nutrients or waste products.

In the present invention, vessel 10 is rotated about a horizontal axis and the process utilizes zero head space of fluid medium within the vessel. The zero head space results in no air bubbles which might cause disruption of the fluid streamlines and thereby subject the culture to adverse shear effects. The preferred means for rotation is a motor assembly (not shown). The motor assembly is fixed to mounting base and is provided with means for attaching to and rotating vessel 10. For instance, attachment means may comprise threadably connecting the vessel 10 to the motor assembly 54 through screw threads on drive shaft 32 corresponding to screw threads on end wall 12 of vessel 10. These screw threads are in a direction such that inadvertent loosening of vessel 10 from the motor assembly 54 due to the movement of rotation is avoided. In addition, a lock nut or similar device may be provided on the drive shaft to prevent unscrewing. However, it is preferred that the attachment means be a series of sprocket gears that cause drive shaft 32, and vessel 10 fixedly attached thereto, to rotate about its horizontal axis.

The means for rotation in yet another embodiment is a roller mechanism having multiple rollers arranged longitudinally in a horizontal plane. The rollers are rotated simultaneously to rotate a reactor vessel laid between the rollers. Such a roller mechanism may be obtained from Stoval Life Science, Inc. but other roller mechanisms that will provide controlled rotation may also be used.

The preferred speed of rotation is in the range of about 2.0 revolutions per minute (rpm) to about 45 rpm. The desired speed of rotation is dependent on the specific dimensions of the vessel 10 and the particular application. For example, for a bioreactor of about 3 to about 5 inches in diameter, with a width of about 0.25 inches, growing BHK-21 cells in a microcarrier culture, the preferred speed of rotation is about 24 rpm. However, in vessels having larger dimensions, the preferred speed of rotation will be decreased to perhaps about 10 to about 15 rpm. It is to be anticipated that the speed of rotation must be adjusted to balance the gravitational force with the centrifugal force caused by that rotation, particularly as larger diameter vessels are used. Further, as cellular masses suspended in the culture medium increase in density with cellular growth, increased rotation rates will be required to maintain those masses in a suspended state.

While the rotation of the vessel 10 may take place by rotating the vessel about the substantially longitudinal central axis in a substantially horizontal plane, it may also take place by rotating the vessel in a plane inclined no more than about 10 degrees from a substantially horizontal plane.

This inclination may become necessary where the flow of medium through the culture chamber is sufficient to carry the growing cells and/or tissues toward the downstream portion of vessel 10.

Vessel 10 may be provided with temperature control means so as to control the temperature of medium within the vessel and the temperature of the medium within the reservoirs 13, 15 and 17 as shown in FIG. 4. In the alternative, the entire bioreactor system may be operated within an enlarged incubator to maintain all of the bioreactor system elements at a desired operating temperature. The desired temperature will be determined by the particular application of vessel 10 and the types of materials being grown therein.

The bioreactor system of the present invention may also be constructed with means for attaching vessel 10 to additional similar vessels, thereby creating a chain or series of bioreactors. The vessels in such a chain are connected to one another by attachment means located on their respective end walls and/or drive shafts. When a chain of bioreactors is formed in this manner, the chain may be attached to a means for rotation at one of its ends for rotation. If a motor assembly is used for rotation of the chain of reactor vessels, access ports 26 should be located on the cylindrical wall 16 of the vessels for easier access. However, if the chain of bioreactors is to be laid on a roller mechanism for rotation, the vessel access ports 26 should be located on the end walls of the vessels.

Another aspect of the present invention is a method for growing cells, cellular aggregates and/or tissues in a bioreactor system comprising filling a vessel, having an unobstructed horizontal longitudinal axis, with a liquid culture medium. Cells, cellular aggregates and/or tissues are suspended in the liquid culture medium and the vessel is rotated about its horizontal longitudinal axis at a rate that suspends the cells in the liquid nutrient medium. A flow of oxygenated nutrient medium is maintained through the vessel to sustain cellular respiration and growth. The rotation of the vessel and the flow of medium is maintained for a period of time to attain desired cell and/or tissue growth.

More specifically, after sterilization, vessel 10 is filled with a fluid nutrient medium, such as those commonly known in the art for growing cells and cellular aggregates, and cells; The nutrient medium may include a variety of materials to sustain the cells, to promote the growth of certain cells, and/or to promote the production or excretion of certain substances by the cells and/or tissues. These materials may include fetal bovine serum, regulatory proteins, salts, sugars, dissolved gases and other materials that combine to form a fluid nutrient medium that approximates blood plasma. Substrate particles such as collagen coated beads and the like may be added to the medium if desired. Further, tissue explant material may be diced and added to the medium either as a substrate for growing other cellular materials or as the as the culturing material for further cell growth.

Once vessel 10 is completely filled with the medium so that no air spaces exist in the vessel, the cells and/or tissues are introduced into the medium and the vessel is rotated as described above. The rate of rotation will depend on the volume of the culture chamber of the vessel and the density of the growing mass of cells and/or tissues. For research purposes, the volume of culture vessel 10 may range from 55 ml. to about 500 mls. For commercial purposes, the volume of the culture vessel may range from about 100 ml to as much as 100 l. As the density of the growing cells will increase with growth, the rate of rotation will likely need to be periodically adjusted to compensate for such changes.

As the materials of cylindrical wall 16 are preferably transparent, the growth of the cells and/or cellular aggregates may be visually monitored. The length of time over which the bioreactor system is operated will vary greatly depending on the application to which the system is being used. When the system is used for diagnostic purposes, vessel may be rotated for only a matter of hours. However, when tissues and large cell masses are to be grown or the secretions of such tissues and/or masses is to be produced, a vessel may be operated over a period of days, weeks or even months.

A continuous flow of oxygen rich nutrient medium is supplied to vessel 10 while the cell, cellular aggregates, tissues and/or organoids are suspended by the rotation of the vessel. The flow rate of the nutrient medium is critical since the culturing of cells and tissues requires a minimum supply of nutrients and oxygen to sustain respiration. The flow rate of the medium depends on the size, and thus, the volume of the culture chamber within the vessel. A higher flow rate being required to provide sufficient oxygen and nutrients to a larger chamber. It is anticipated that the flow of medium into the vessel may be as high as 10 ml/min. However, at this flow rate the filter elements of the vessel are likely to clog and periodic reversing the direction of medium flow may be required to back flush the clog from the filters. In the preferred method, the flow rate will vary between 2 and 3 ml/min.

Temperature control is also essential to maintaining culture chamber 30 at an optimum temperature for cell growth. Preferably, the desired temperature will be maintained by operating the entire bioreactor system within an incubator. In the alternative, temperature control means may be utilized in the medium reservoirs and within vessel 10. The temperature will preferably range from about 35° C. to about 40° C. for mammalian cells.

When the desired level of growth or production has been reached, rotation is stopped, the vessel access ports are opened and the cellular materials removed. If vessel 10 is made of sterilizable materials the vessel may be emptied and sterilized for future use. If disposable, the vessel and any undesirable contents are destroyed.

Another aspect of the present invention is to provide a method for filtering waste materials from fluids. As shown in FIG. 11, organoids of liver, kidney, pancreatic and other tissues and/or cells may be suspended in the rotating culture chamber 30. A fluid containing waste materials or toxins is added to the fluid nutrient medium passing into the reactor vessel and through filter element 34. As the fluid medium passes through the culture chamber, the organoids suspended in the chamber filter the waste material from the fluid utilizing various cellular mechanisms. The cellular mechanisms carried out by these organoids are the same as or similar to the mechanisms used by human organs to remove toxins and other waste materials from the human body.

There is a limit to the quantity of materials that can be removed from the fluid flowing through a single reactor vessel. As the ability of the suspended organoids to filter toxins becomes exhausted, the organoids will frequently expire. Therefore, it is preferable that the bioreactor system will have multiple vessels arranged in series so that periodically, a vessel containing depleted organoids may be removed and replaced with a vessel containing fresh organoids. The fluid communication between the vessels in such a series allows for more efficient filtering and further allows the filtering process to continue without significant interruption when the organoids in a vessel need to be replaced.

In another aspect of the invention, the reactor vessel of the present invention may be used as a method of carrying out various diagnostic procedures. By way of example only, the reactor vessel of the present invention may be used to test new chemical agents for treating various diseases or cancers. In particular, a reactor vessel that has been subdivided into a number of sub-chambers may contain diseased or cancerous tissues in one sub-chamber while liver, kidney and other tissues may be suspended in the other sub-chambers. The fluid medium containing a chemical agent for treating the diseased tissues is circulated through the vessel for a desired period of time to determine the affects the agent. The significance of this procedure is that the action of the agent on the diseased or cancerous tissue may be monitored in the presence of various organ tissues that may counteract the affects of the agent or that may be adversely affected by the agent.

As noted, the bioreactor system of the present invention can be used for a variety of applications. In terms of research, the reactor vessel may be used in researching cancer, HIV, tissue modeling, genetics, tissue maintenance, virology, extracellular matrix interactions, signal transduction and protein discoveries. In terms of the tissue regeneration, the reactor vessel can be used to generate bone marrow, liver, pancreas, skin, heart, nerve, cartilage, kidney, blood and blood vessel tissues. Likewise, the reactor vessel may be used to produce various tissues, pharmaceuticals, diagnostic agents, vaccines, cellular aggregates and organoids.

Cells and tissues that can be grown in the bioreactor system of the present invention include human keratinocytes, epithelial and fibroblast cells of small intestine, lymphocytes, melanocytes, embryonic cells, osteoblasts, hepatocytes, bone marrow and bone marrow stem cells. Various cancers that can be produced in the reactor vessel of the present invention include neuroblastoma, breast, prostate, lung, melanoma, kidney, and ovarian cancers and adenocarcinoma. Examples of viruses that can be grown in the reactor vessel of the present invention include AIDS/HIV, ebola, HHV8-Kaposi's Sarcoma, influenza, Epstine Barr virus, Monkey pox and Norwalk.

From the foregoing it will be seen that this invention is one well adapted to attain all of the ends and objects hereinabove set forth, together with other advantages which are obvious and which are inherent to the apparatus and structure.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative and not in a limiting sense.

What is claimed is:

1. A method for filtering biological waste material and toxins from a fluid medium using cellular filtering, comprising the steps of:

providing a rotatable cylindrical vessel having a filter chamber with an unobstructed longitudinal axis;

filling the vessel with an oxygen rich fluid culture medium;

introducing live organoids into the medium;

maintaining a flow of oxygen rich fluid culture medium through the vessel to provide oxygen and materials to the living organoids and to remove cellular metabolic waste;

rotating the vessel to suspend the organoids in the medium; and passing a fluid containing a waste material and toxins through the chamber wherein the suspended organoids remove the waste material and toxins from said fluid using cellular mechanisms.

2. The method of claim 1, further comprising the step of providing additional cylindrical vessels in series with fluid communication between the vessels.

3. The method of claim 2, further comprising the step of periodically removing a vessel containing depleted organoids from the series and adding a vessel containing fresh organoids to the series.

* * * * *